US007871602B2

(12) United States Patent
Dassanayake et al.

(10) Patent No.: US 7,871,602 B2
(45) Date of Patent: *Jan. 18, 2011

(54) USE OF BIS-AMINES TO ENHANCE THE ANTIMICROBIAL ACTIVITY OF AQUEOUS COMPOSITIONS

(75) Inventors: Nissanke L. Dassanayake, Arlington, TX (US); Thomas Christopher Carey, Fort Worth, TX (US); Ronald L. Schlitzer, Fort Worth, TX (US); David L. Meadows, Colleyville, TX (US)

(73) Assignee: Alcon, Inc., Hunenberg (CH)

( * ) Notice: Subject to any disclaimer, the term of this patent is extended or adjusted under 35 U.S.C. 154(b) by 0 days.

This patent is subject to a terminal disclaimer.

(21) Appl. No.: 12/244,907

(22) Filed: Oct. 3, 2008

(65) Prior Publication Data

US 2009/0030085 A1    Jan. 29, 2009

Related U.S. Application Data

(63) Continuation of application No. 11/008,027, filed on Dec. 9, 2004, now Pat. No. 7,445,771.

(60) Provisional application No. 60/528,287, filed on Dec. 9, 2003.

(51) Int. Cl.
*A61K 31/74* (2006.01)

(52) U.S. Cl. .................. 424/78.04; 564/503; 564/504; 564/505; 564/506; 564/507; 564/508; 564/509; 564/510; 564/511; 564/512; 514/669; 514/671; 514/673

(58) Field of Classification Search ........................ None
See application file for complete search history.

(56) References Cited

U.S. PATENT DOCUMENTS

| | | | |
|---|---|---|---|
| 2,246,524 | A | 6/1941 | Kyrides |
| 3,206,462 | A | 9/1965 | McCarty |
| 3,294,689 | A | 12/1966 | Pierce |
| 3,729,564 | A | 4/1973 | Chang et al. |
| 3,855,297 | A | 12/1974 | Diana et al. |
| 4,004,030 | A | 1/1977 | Schwarzmann et al. |
| 4,119,668 | A | 10/1978 | Diana et al. |
| 5,631,005 | A | 5/1997 | Dassanayake et al. |
| 5,741,817 | A | 4/1998 | Chowhan et al. |
| 5,817,277 | A | 10/1998 | Maurey-Mckee et al. |
| 5,900,213 | A | 5/1999 | Dassanayake et al. |
| 6,319,464 | B1 | 11/2001 | Asgharian |
| 6,503,497 | B2 | 1/2003 | Chowhan et al. |
| 6,664,294 | B1 | 12/2003 | Park et al. |
| 6,939,840 | B2 | 9/2005 | Lichtenberg et al. |
| 7,445,771 | B2 * | 11/2008 | Dassanayake et al. ..... 424/78.04 |
| 2002/0122831 | A1 | 9/2002 | Mowrey-Mckee |

FOREIGN PATENT DOCUMENTS

| DE | 969 699 | 7/1958 |
|---|---|---|
| DE | 2113208 | 9/1972 |
| GB | 1327315 | 8/1973 |
| GB | 1422704 | 10/1978 |
| JP | 52-10423 | 1/1977 |
| JP | 10-273403 | 10/1998 |
| JP | 2002-316926 | 10/2002 |
| JP | 2003-192589 | 7/2003 |
| JP | 2003-300871 | 10/2003 |
| WO | 9425426 | 11/1994 |
| WO | 9704308 | 2/1997 |
| WO | 02/23990 | 3/2002 |

OTHER PUBLICATIONS

Database CAPLUS on STN, Acc. No. 1955:64781, Hill et al., Journal of the American Chemical Society (1954), 76, p. 3548-3550 (abstract).*
Database CAPLUS on STN, Acc. No. 1996:198207, Rehse et al., Archiv der Pharmazie (1996), 329(3), p. 155-160 (abstract).*
Adzamli, et al.; "Developmetnt of phosphonate derivatives of gadolinium chelates for NMR imaging of calcified soft tissues"; Journal of Medicinal Chemistry; vol. 32; No. 1; pp. 139-144; 1989.
Hill, et al.; "Nitrogen-substituted-3,4-dihydroxypyrrolidines"; J. Amer. Chem. Soc.; vol. 76; pp. 3548-3550; 1954.
Database Beilstein [Online] Feb. 27, 1989 XP-002335010 abstract and Hill et al., Journal of the American Chemnical Society, vol. 76, (1954), p. 3548.
Extended European Search Report for corresponding EP application No. EP 08021320.0 with mailing date May 15, 2009.
Rehse et al., "Antiaggregatorische und anticoagulant Eigenschaften von Oligoaminen, 6. Mitt.: Oligohydroxyalkandiamine", Archiv Der Pharmazie, VCH Verlagsgesellschaft MBH, Weinheim, DE, vol. 320, No. 11, Jan. 1, 1987, pp. 1155-1161, XP008058598 ISSN: 0365-6233 p. 1156: "Tabelle 1", compounds 15-17; see also p. 1160.
Rehse et al., "Platelet Aggregation Inhibiting and Anticoagulant Effects of Oligoamines, Part 32. Antimicrobial Effects of Oligoamines", Archiv Der Pharmazie, VCH Verlagsgesellschaft MBH, Weinheim, DE, vol. 329, Nov. 3, 1996, pp. 155-160, XP00253576 p. 156, Table 1, compounds 6b and 6c.
Star et al., "Novel Dioxadiazadecalin Podands and Their Heavy Metal Ion Complexes", European Journal of Organic Chemistry, 2001, pp. 729-734, XP002523575 p. 730, compound 11 and compound 13; p. 732, "Experimental section", compound 11.
Database HCAPLUS on STN, Acc. No. 1977:189190, Kolaczinski et al., abstract (corresponding record for JP 52-010423).
Database HCAPLUS on STN, Acc. No. 2002:240501, Lichtenberg et al., abstract (corresponding record for WO 02/23990).
Database HCAPLUS on STN, Acc. No. 1960:71506, Menzi et al., abstract (corresponding record for DE 969 699).
Database HCAPLUS on STN, Acc. No. 1964:16531, UHLIG and DORN, Journal fuer Praktische Chemie, abstract.

(Continued)

*Primary Examiner*—Brian J Davis
(74) *Attorney, Agent, or Firm*—Michael D. Rein

(57) ABSTRACT

The use of bis-amines to enhance the antimicrobial activity of pharmaceutical compositions is described. The bis-amines are particularly useful for enhancing the antimicrobial activity of aqueous ophthalmic compositions, such as artificial tears or ocular lubricants, and solutions for disinfecting contact lenses.

16 Claims, No Drawings

OTHER PUBLICATIONS

Translated corresponding Japanese Patent Application No. 2006-544001 Office Action dated Jul. 23, 2010.

UHLIG and DORN; Journal fuer Praktische, 1963, 21(5-6), pp. 266-271.

* cited by examiner

US 7,871,602 B2

USE OF BIS-AMINES TO ENHANCE THE ANTIMICROBIAL ACTIVITY OF AQUEOUS COMPOSITIONS

CLAIM FOR PRIORITY

The present application is a continuation application of, and claims priority to, U.S. patent application Ser. No. 11/008,027 filed Dec. 9, 2004, now U.S. Pat. No 7,445,771, which claims benefit of U.S. Provisional Application Ser. No. 60/528,287 filed Dec. 9, 2003.

BACKGROUND OF THE INVENTION

The present invention is directed to the use of bis-amines to enhance the antimicrobial activity of aqueous compositions, such as pharmaceutical compositions. The invention is particularly directed to the field of ophthalmic compositions.

Many pharmaceutical compositions are required to be sterile (i.e., free of bacteria, fungi and other pathogenic microorganisms). Examples of such compositions include: solutions and suspensions that are injected into the bodies of humans or other mammals; creams, lotions, solutions or other preparations that are topically applied to wounds, abrasions, burns, rashes, surgical incisions, or other conditions where the skin is not intact; and various types of compositions that are applied either directly to the eye (e.g., artificial tears, irrigating solutions, and drug products), or are applied to devices that will come into contact with the eye (e.g., contact lenses).

The foregoing types of compositions can be manufactured under sterile conditions via procedures that are well known to those skilled in the art. However, once the packaging for the product is opened, such that the composition is exposed to the atmosphere and other sources of potential microbial contamination (e.g., the hands of a human patient), the sterility of the product may be compromised. Such products are typically utilized multiple times by the patient, and are therefore frequently referred to as being of a "multi-dose" nature.

Due to the frequent, repeated exposure of multi-dose products to the risk of microbial contamination, it is necessary to employ a means for preventing such contamination from occurring. The means employed may be (1) a chemical agent that prevents the proliferation of microbes in the composition, which is referred to herein as an "antimicrobial preservative"; or (2) a packaging system that prevents or reduces the risk of microbes reaching the pharmaceutical composition within a container.

Multi-dose ophthalmic compositions generally must include an anti-microbial agent to prevent contamination of the compositions by bacteria, fungi and other microbes. Such compositions may come into contact with the cornea either directly or indirectly. The cornea is particularly sensitive to exogenous chemical agents. Consequently, in order to minimize the potential for harmful effects on the cornea, it is necessary to use anti-microbial agents that are relatively non-toxic to the cornea, and to use such agents at the lowest possible concentrations (i.e., the minimum amounts required in order to perform their anti-microbial functions).

Balancing the anti-microbial efficacy and potential toxicological effects of anti-microbial agents is sometimes difficult to achieve. More specifically, the anti-microbial agent concentration necessary for the preservation of ophthalmic formulations from microbial contamination or for the disinfection of contact lenses may create the potential for toxicological effects on the cornea and/or other ophthalmic tissues. Using lower concentrations of the anti-microbial agents generally helps to reduce the potential for such toxicological effects, but the lower concentrations may be insufficient to achieve the required level of biocidal efficacy (e.g., antimicrobial preservation or disinfection).

The use of an inadequate level of antimicrobial preservation may create the potential for microbial contamination of the compositions and ophthalmic infections resulting from such contaminations. This is also a serious problem, since ophthalmic infections involving *Pseudomonas aeruginosa* or other virulent microorganisms can lead to loss of visual function or even loss of the eye.

Thus, there is a need for a means of enhancing the activity of anti-microbial agents so that very low concentrations of the agents can be utilized without increasing the potential for toxicological effects or subjecting patients to unacceptable risks of microbial contamination and resulting ophthalmic infections.

Compositions for treating contact lenses and other types of ophthalmic compositions are generally formulated as isotonic, buffered solutions. One approach to enhancing the anti-microbial activity of such compositions is to include multi-functional components in the compositions. In addition to performing their primary functions, such as cleaning or wetting contact lens surfaces (e.g., surfactants), buffering the compositions (e.g., borate), or chelating undesirable ions (e.g., EDTA), these multi-functional components also serve to enhance the overall anti-microbial activity of the compositions. For example, ethylenediaminetetraacetic acid and the monosodium, disodium and trisodium salts thereof (collectively referred to herein as "EDTA") has been widely used for many years in ophthalmic products, particularly products for treating contact lenses. EDTA has been used in such products for various purposes, but particularly for its supplemental anti-microbial activity and as a chelating agent. The inclusion of EDTA in contact lens care products and other ophthalmic compositions enhances the anti-microbial efficacy of chemical preservatives contained in such compositions, particularly the efficacy of those preservatives against gram negative bacteria.

The following publications may be referred to for further background regarding the use of multi-functional components to enhance the antimicrobial activity of ophthalmic compositions:
1. U.S. Pat. No. 5,817,277 (Mowrey-McKee, et al; tromethamine);
2. U.S. Pat. No. 6,503,497 (Chowhan, et al.; borate/polyol complexes);
3. U.S. Pat. No. 5,741,817 (Chowhan, et al.; low molecular weight amino acids such as glycine);
4. U.S. Pat. No. 6,319,464 (Asgharian; low molecular weight amino alcohols); and
5. U.S. Patent Application Publication No. US 2002/0122831 A1 (Mowrey-McKee, et al.; bis-aminopolyols).

SUMMARY OF THE INVENTION

The present invention is directed to the use of bis-amines to enhance the antimicrobial activity of compositions. The enhancement of antimicrobial activity is useful in preserving the compositions from microbial contamination, by preventing proliferation of microorganisms in the compositions. The invention may also be employed to increase the ability of the composition to kill microorganisms that come in contact with the composition, such as in the case of topical antiseptics and disinfectants.

The present invention is particularly directed to the use of bis-amines to enhance the antimicrobial activity of aqueous ophthalmic compositions. The bis-amines may be used without other antimicrobial agents, but will generally be employed together with other agents having mild to moderate levels of antimicrobial activity, so as to produce a preservative system that is effective in preventing microbial contamination of compositions in the absence of conventional antimicrobial preservatives, such as benzalkonium chloride ("BAC") or polyquarternium-1. Compositions that are preserved by means of such systems and do not contain a conventional antimicrobial preservative are referred to herein as being "self-preserved".

The bis-amines described herein may also be utilized to enhance the antimicrobial activity of ophthalmic antiseptic or disinfectant compositions, such as solutions utilized to disinfect contact lenses.

DETAILED DESCRIPTION OF THE INVENTION

The bis-amines utilized in the present invention have the following formula:

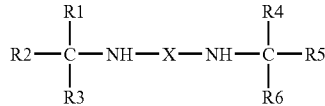
(I)

wherein:
$R_1, R_2, R_3, R_4, R_5$ and $R_6$ are independently selected from the group consisting of:
H; —CH$_2$OH; and C$_1$-C$_{12}$ straight or branched alkyl or alkenyl, optionally containing one or more heteroatoms (e.g., oxygen); provided that no more than one of $R_1$, $R_2$ and $R_3$ is —CH$_2$OH, and no more than one of $R_4$, $R_5$ and $R_6$ is —CH$_2$OH; and
X is selected from the group consisting of:
C$_1$-C$_{16}$ saturated or unsaturated alkylene, optionally containing one or more heteroatoms (e.g., oxygen);
(—CH$_2$—)$_w$CHOH—CHOH(—CH$_2$—)$_w$, wherein w is a whole number of from 1 to 6 and the hydroxy groups are in either cis or trans configurations;
(—CH$_2$—O—CH$_2$—)$_x$, wherein x is a whole number of from 1 to 6;
(—CH═CH—)$_y$ (alkene), wherein y is a whole number of from 1 to 6; and
(—C≡C—)$_z$ (alkyne), wherein z is a whole number of from 1 to 6.

The present invention also encompasses pharmaceutically acceptable salts of the compounds of formula (I).

The —CH$_2$OH groups at the $R_1$-$R_6$ positions affect the hydrophobicity of the compounds of formula (I). It has been determined that if more than two —CH$_2$OH groups are present, the hydrophobicity is decreased to an extent such that the antimicrobial activity of the compounds is diminished.

The preferred bis-amines of formula (I) are the compounds wherein:
one of $R_1$, $R_2$ or $R_3$ is —CH$_2$OH, one of $R_3$, $R_4$ and $R_5$ is —CH$_2$OH, and the remainder of the $R_1$-$R_6$ groups are C$_1$-C$_5$ straight or branched alkyl, preferably methyl; and
X is selected from the group consisting of: (—CH$_2$—)$_n$, wherein n is a whole number of from 3 to 6; and the other X groups identified above, wherein w, x, y and z are 1.

Examples of the most preferred bis-amines are shown below:
1. Compound No. AL-38571

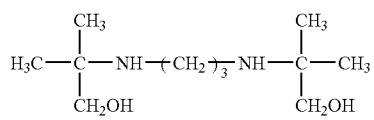

(1,3-bis[(dimethyl,hydroxymethyl)methylamino]propane;
2. Compound No. AL-39114

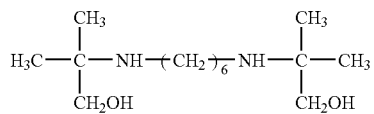

1,6-bis[(dimethyl, hydroxymethyl)methylamino]hexane;
3. Compound No. AL-39503

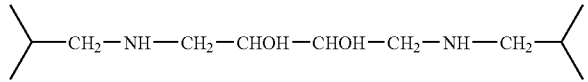

1,4-bis[isobutylamino]2,3-dihydroxy butane;
4. Compound No. AL-39504

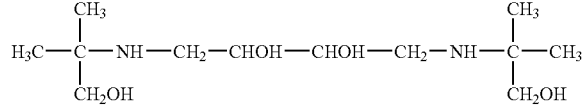

1,4-bis[(dimethyl,hydroxymethyl)methylamino]2,3-hydroxy butane; and
5. Compound No. AL-39586

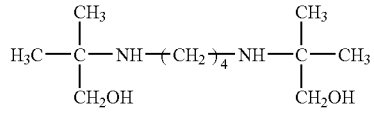

1,4-bis[(dimethyl, hydroxymethyl)methylamino]butane.

The bis-amines of formula (I) can be synthesized using procedures known to those skilled in the art. Representative reaction schemes are described in Examples 1-4, below.

The amount of one or more bis-amines of formula (I) required to enhance the antimicrobial activity of particular formulations can be readily determined by persons skilled in the art. The concentration required will depend on the particular bis-amine(s) selected, the presence or absence of other ingredients that have antimicrobial activity (e.g., anti-microbial agents, chelating agents, buffering agents or tonicity agents), and the function of the anti-microbial agents contained in the ophthalmic compositions (e.g., preservation of the compositions from microbial contamination, or disinfection of contact lenses). The concentration required to enhance the antimicrobial activity of ophthalmic compositions is referred to herein as "an effective amount". The concentration will generally be in the range of 0.01 to 2.0 weight/volume percent ("w/v %"), preferably 0.1 to 1.0 w/v %.

The levels of antimicrobial activity required to preserve ophthalmic compositions from microbial contamination or to disinfect contact lenses are well known to those skilled in the art, based both on personal experience and official, published standards, such as those set forth in the United States Pharmacopoeia ("USP") and similar publications in other countries.

As indicated above, the bis-amines described above are preferably used in combination with borate or borate/polyol buffer systems. As used herein, the term "borate" includes boric acid, salts of boric acid, other pharmaceutically acceptable borates, and combinations thereof. The following borates are particularly preferred: boric acid, sodium borate, potassium borate, calcium borate, magnesium borate, manganese borate, and other such borate salts.

As used herein, the term "polyol" includes any compound having at least one hydroxyl group on each of two adjacent carbon atoms that are not in trans configuration relative to each other. The polyols can be linear or cyclic, substituted or unsubstituted, or mixtures thereof, so long as the resultant complex is water soluble and pharmaceutically acceptable. Examples of such compounds include: sugars, sugar alcohols, sugar acids and uronic acids. Preferred polyols are sugars, sugar alcohols and sugar acids, including, but not limited to: mannitol, glycerin, xylitol and sorbitol. Especially preferred polyols are mannitol and sorbitol; most preferred is sorbitol.

The use of borate-polyol complexes in ophthalmic compositions is described in U.S. Pat. No. 6,503,497 (Chowhan); the entire contents of which are hereby incorporated in the present specification by reference. The compositions of the present invention preferably contain one or more borates in an amount of from about 0.01 to about 2.0% w/v, more preferably from about 0.3 to 1.2% w/v, and one or more polyols in an amount of from about 0.01 to 5.0% w/v, more preferably from about 0.6 to 2.0% w/v.

The bis-amines described herein may be included in various types of ophthalmic compositions to enhance anti-microbial activity. Examples of such compositions include: ophthalmic pharmaceutical compositions, such as topical compositions used in the treatment of glaucoma, infections, allergies or inflammation; compositions for treating contact lenses, such as cleaning products and products for enhancing the ocular comfort of patients wearing contact lenses; and various other types of compositions, such as ocular lubricating products, artificial tears, astringents, and so on. The compositions may be aqueous or non-aqueous, but will generally be aqueous.

In addition to the bis-amines described above, the compositions of the present invention may contain one or more anti-microbial agents to preserve the compositions from microbial contamination and/or disinfect contact lenses. The invention is not limited relative to the types of antimicrobial agents that may be utilized. The preferred biocides include: polyhexamethylene biguanide polymers ("PHMB"), polyquarternium-1, and the amino biguanides described in co-pending U.S. patent application Ser. No. 09/581,952 and corresponding International (PCT) Publication No. WO 99/32158, the entire contents of which are hereby incorporated in the present specification by reference.

The most preferred amino biguanide is identified in U.S. patent application Ser. No. 09/581,952 as "Compound Number 1". This compound has the following structure:

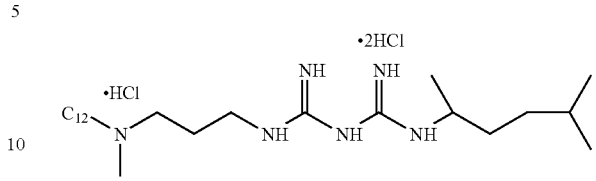

It is referred to below by means of the code number "AL-8496".

Amidoamines and amino alcohols may also be utilized to enhance the antimicrobial activity of the compositions described herein. The preferred amidoamines are myristamidopropyl dimethylamine ("MAPDA") and related compounds described in U.S. Pat. No. 5,631,005 (Dassanayake, et al.). The preferred amino alcohols are 2-amino-2-methyl-1-propanol ("AMP") and other amino alcohols described in U.S. Pat. No. 6,319,464 (Asgharian). The entire contents of the '005 and '464 patents are hereby incorporated in the present specification by reference.

The compositions of the present invention may also contain a wide variety of other ingredients, such as tonicity-adjusting agents (e.g., sodium chloride or mannitol), surfactants (e.g., anionic surfactants, such as RLM 100, and nonionic surfactants, such as the poloxamines sold under the name "Tetronic®" and the poloxamers sold under the name "Pluronic®"), and viscosity adjusting agents. The present invention is not limited with respect to the types of ophthalmic compositions in which the bis-amines described herein are utilized.

The ophthalmic compositions of the present invention will be formulated so as to be compatible with the eye and/or contact lenses to be treated with the compositions. The ophthalmic compositions intended for direct application to the eye will be formulated so as to have a pH and tonicity which are compatible with the eye. This will normally require a buffer to maintain the pH of the composition at or near physiologic pH (i.e., 7.4) and may require a tonicity agent to bring the osmolality of the composition to a level at or near 210-320 milliosmoles per kilogram (mOsm/kg). The formulation of compositions for disinfecting and/or cleaning contact lenses will involve similar considerations, as well as considerations relating to the physical effect of the compositions on contact lens materials and the potential for binding or absorption of the components of the composition by the lens. The compositions will generally be formulated as sterile aqueous solutions.

The following examples are presented to further illustrate selected embodiments of the present invention.

EXAMPLE 1

Synthesis of Compound No. AL-38571: 1,3-bis[(dimethyl,hydroxymethyl)methylamino]propane The foregoing compound was synthesized by means of the reaction scheme shown below:

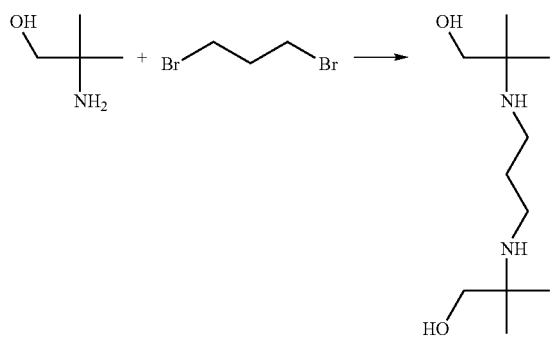

2-Amino-2-methyl-propane (1.78 gm, 2 eq.) and 1,3-dibromopropane (2.02 gm, 1 eq.) was heated for 1 hr. The product obtained was washed with ethanol, followed by ether (3 times). The solid obtained was dried under vacuum to yield 1,3-bis[(dimethyl,hydroxymethyl)methylamino]propane. Yield 800 mg. The compound was characterized by Mass Spec. and N.M.R.

EXAMPLE 2

Synthesis of Compound No. AL-39504: 1,4-bis[(dimethyl,hydroxymethyl)methylamino]2,3-hydroxy butane dihydrochloride The foregoing compound was synthesized by means of the reaction scheme shown below:

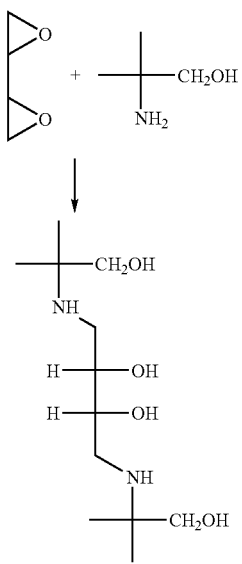

2-Methyl-2-amino-propanol (6.2 g, 69.5 mmoles) was heated with 1,3-butadiene diepoxide (2.67 g, 31 mmoles) for 48 hrs. The solution was allowed to cool and the excess starting materials were then removed in vacuo. The residue was purified by recrystallization as the oxalic acid salt: the residue was treated with oxalic acid (5.5 gm, 61 mmoles) and the resulting solid was recrystallized from hot methanol and resultant crystals were washed several times with cold methanol. The oxalate salt was then converted into the free base by ion exchange chromatography using Amberlite IR-120H$^+$ resin.

The product loaded on the resin in water and was eluted from the resin using 3M ammonium hydroxide. The eluate was evaporated to dryness in a rotary evaporator. The resulting gum was dissolved in methanol (50 ml) and concentrated HCl was added dropwise to the methanol solution until acidic pH was obtained. The product was then evaporated to dryness to yield a brown amorphous solid 1,4-bis[(dimethyl,hydroxymethyl)methylamino]2,3-hydroxy butane dihydrochloride (4.2 gm, 51% yield). The purity of compound was confirmed by ESI Mass Spectroscopy and $^1$H NMR analysis.

EXAMPLE 3

Compound No. AL-39503: 1,4-bis[isobutyl amino]2,3-hydroxy butane dihydrochloride The foregoing compound was synthesized as follows:

Isobutyl amine (5.0 g, 68 mmoles) was heated with 1,3-butadiene diepoxide (2.95 g, 34 mmoles) for 48 hrs. The solution was allowed to cool and the excess starting materials were then removed in vacuo. The resulting amorphous solid was dissolved in methanol (50 ml). Concentrated HCl was added to the methanol solution until acidic pH was reached. The solution was evaporated to dryness to yield a white solid. The product was then recrystallized from hot ethanol to yield 1,4-bis[isobutyl amino]2,3-hydroxy butane dihydrochloride (3.0 g, 38% yield). The purity of compound was confirmed by ESI Mass Spectroscopy and $^1$H NMR analysis.

EXAMPLE 4

Compound No. AL-39586: 1,4-bis[(dimethyl,hydroxymethyl)methylamino]butane

The foregoing compound was synthesized by means of the reaction scheme shown below:

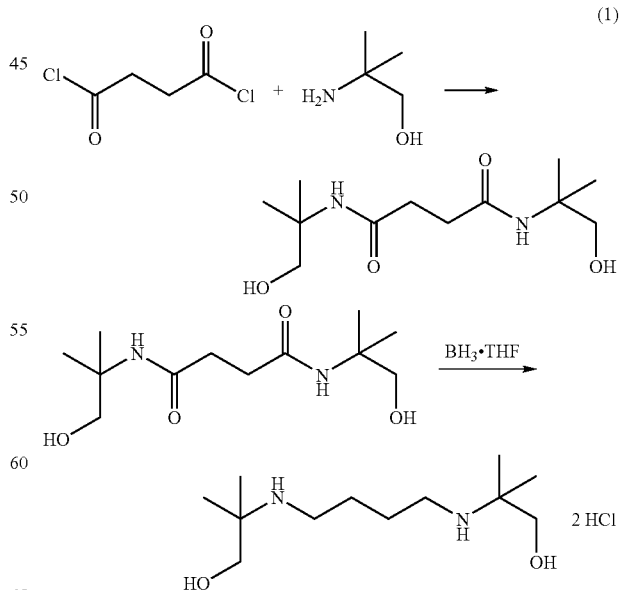

A solution of succinyl chloride (4.18 g, 27 mmol) in $CH_2Cl_2$ (40 mL) was added dropwise at 0° C. (over a period of 1 hour) to a solution of 2-amino-2-methyl-1-propanol (14.41 g, 0.16 mol) in $CH_2Cl_2$ (150 mL). The reaction mixture was stirred at room temperature for 5 hours. After the solvent had been removed under a Büchi rotary evaporator, acetone (400 mL) was added to the residue, and the resulting mixture was stirred for 1 hour at room temperature. The solid was then filtered off, the filtrate was concentrated under reduced pressure, and $CH_2Cl_2$ (30 mL) was added to the concentrate, which was obtained as oily solids. The solid precipitate was filtered and washed with cold $CH_2Cl_2$ (10 mL), followed by hexane. The filter cake was dried under vacuum. The crude product was purified (to remove small amounts of the hydrochloride salt of 2-amino-2-methyl-1-propanol) by silica gel (120 grams) column chromatography eluting with 15% MeOH—$CH_2Cl_2$ to afford 4.70 g (67%) of (1) as a white powder. (This intermediate compound is referred to below as "Compound A".)

To a suspension of Compound A (4.90 g, 18.82 mmol) in THF (100 mL) was added slowly at 0° C. a solution of borane-THF complex (1 M in THF; 75.3 mL). The reaction mixture was heated at reflux overnight. After the reaction mixture had been cooled to 0° C., a 6 N HCl solution (17 mL) was slowly added. The resulting suspension was stirred at room temperature for 1 hour, and the precipitate was filtered and washed with THF to give the dihydrochloride salt as solid. After fresh THF (50 mL) had been added to the solid, the resulting suspension was heated at reflux and then cooled to room temperature, following stirring for an additional 3 hours. The precipitate was filtered, and the filter cake was dried in vacuo to give 5.34 g (93%) of the 2.HCl salt of 1,4-bis-[(dimethyl,hydroxymethyl)methylamino]butane as a white powder. The compound was characterized by Mass Spec and N.M.R.

EXAMPLE 5

The formulations shown in Table 1 below were prepared to evaluate the ability of the bis-amines of formula (I) to enhance the antimicrobial activity of ophthalmic compositions, particularly artificial tear solutions:

The formulations described in Table 1 were prepared as follows:

HPMC Solution:

1. In a 250 mL Pyrex media bottle, add the correct amount of 2% HPMC stock solution.
2. Autoclave at 121° C. for 30 minutes.
3. Hold the autoclaved solution for later compounding.

Buffer Vehicle:

1. In a 250 mL beaker, add the remaining formulation chemicals for a 200 mL batch using only 150 mL of purified water.
2. Measure the pH and adjust to 7.9 with NaOH/HCl.
3. QS to 100% (150 mL) with purified water.
4. Filter the solution using a 0.2 μm CA filter unit.

Final Formulation:

1. Slowly add the filtered buffer vehicle to the autoclaved HPMC stock solution.
2. Allow the solution to mix well.

EXAMPLE 6

The antimicrobial activity of the solutions described in Example 5 was evaluated by means of a standard microbiological analysis (i.e., USP 26 Antimicrobial Effectiveness Test). The test samples were challenged with standardized suspensions of *Aspergillus niger*, *Candida albicans*, *Escherichia coli*, *Pseudomonas aeruginosa*, and *Staphylococcus aureus*, and the number of surviving microorganisms was determined at 7, 14 and 28 days. The results are presented in Table 2 below:

TABLE 1

| | Formulation Numbers/Concentrations (% w/v) | | | | | | |
|---|---|---|---|---|---|---|---|
| Component | 10581-37A | 10581-37B | 10581-37C | 10581-37D | 10581-37E | 10581-37F | 10581-37G |
| Dextran 70 | 0.1 | 0.1 | 0.1 | 0.1 | 0.1 | 0.1 | 0.1 |
| HPMC | 0.3 | 0.3 | 0.3 | 0.3 | 0.3 | 0.3 | 0.3 |
| Propylene Glycol | 0.3 | 0.3 | 0.3 | 0.3 | 0.3 | 0.3 | 0.3 |
| Boric acid | 0.8 | 0.8 | 0.8 | 0.8 | 0.8 | 0.8 | 0.8 |
| Sorbitol | 1.4 | 1.4 | 1.4 | 1.4 | 1.4 | 1.4 | 1.4 |
| Sodium chloride | 0.1 | 0.1 | 0.1 | 0.1 | 0.1 | 0.1 | 0.1 |
| Potassium chloride | 0.12 | 0.12 | 0.12 | 0.12 | 0.12 | 0.12 | 0.12 |
| Calcium chloride | 0.0053 | 0.0053 | 0.0053 | 0.0053 | 0.0053 | 0.0053 | 0.0053 |
| Magnesium chloride | 0.0064 | 0.0064 | 0.0064 | 0.0064 | 0.0064 | 0.0064 | 0.0064 |
| Zinc chloride | 0.00015 | 0.00015 | 0.00015 | 0.00015 | 0.00015 | 0.00015 | 0.00015 |
| AMP (95%) | 0.588 | — | — | — | — | — | — |
| AL-38571A | — | 1.5 (51.5 mM) | 1.0 (34.3 mM) | 0.5 (17.2 mM) | — | — | — |
| AL-39114A | — | — | — | — | 1.124 (51.5 mM) | 0.742 (34 mM) | 0.37 (17 mM) |
| pH | 7.9 | 7.9 | 7.9 | 7.9 | 7.9 | 7.9 | 7.9 |

TABLE 2

| Organism | Time (days) | Formulation Number/Log$_{10}$ Reduction of Survivors | | | | | | |
|---|---|---|---|---|---|---|---|---|
| | | 10581-37A | 10581-37B | 10581-37C | 10581-37D | 10581-37E | 10581-37F | 10581-37G |
| A. niger | 7 | 1.7 | 1.9 | 1.9 | 1.6 | 2.0 | 1.9 | 1.8 |
| $9.5 \times 10^{5a}$ | 14 | 2.2 | 2.9 | 2.6 | 2.6 | 2.5 | 2.4 | 2.3 |
| | 28 | 2.6 | 3.6 | 3.5 | 4.2 | 2.9 | 2.8 | 2.7 |
| C. albicans | 7 | 0.4 | 0.4 | 0.4 | 0.2 | 0.6 | 0.4 | 0.2 |
| $2.0 \times 10^6$ | 14 | 1.4 | 1.2 | 1.1 | 0.3 | 1.7 | 1.4 | 1.0 |
| | 28 | 2.6 | 1.8 | 2.0 | 1.2 | 2.8 | 2.6 | 1.8 |
| E. coli | 7 | _5.8$^b$_ | _5.8_ | 4.3 | −0.4 | 4.8 | 4.0 | 2.9 |
| $5.9 \times 10^5$ | 14 | _5.8_ | _5.8_ | _5.8_ | 0.6 | _5.8_ | _5.8_ | _5.8_ |
| | 28 | _5.8_ | _5.8_ | _5.8_ | 0.0 | _5.8_ | _5.8_ | _5.8_ |
| P. aeruginosa | 7 | _6.0_ | _6.0_ | 4.4 | −0.5 | 4.6 | 1.3 | −0.3 |
| $9.0 \times 10^5$ | 14 | _6.0_ | _6.0_ | 4.5 | −0.6 | 4.4 | 1.0 | −0.1 |
| | 28 | _6.0_ | _6.0_ | 4.4 | −0.3 | 4.6 | 0.7 | 0.9 |
| S. aureus | 7 | 4.5 | 3.9 | 1.6 | 0.6 | 3.4 | 2.8 | 2.4 |
| $1.4 \times 10^6$ | 14 | _6.1_ | _6.1_ | 3.0 | 3.4 | _6.1_ | _6.1_ | 5.1 |
| | 28 | _6.1_ | _6.1_ | _6.1_ | _6.1_ | _6.1_ | _6.1_ | _6.1_ |

$^a$Inoculum control
$^b$Underlined number indicates no survivors (<10 CFU/mL) recovered The results demonstrate overall preservative efficacy against the organisms tested at 51 mM concentrations for both compounds evaluated (i.e., AL-38571A and AL-39114A). The results also indicate that there was a dose response for both compounds when tested at 34 mM and 17 mM concentrations in this vehicle. (Solutions D, F, and G, which contained these lower concentrations of compounds, did not satisfy the USP preservative efficacy requirements.)

EXAMPLE 7

The formulations shown in Table 3 below were prepared in accordance with procedures similar to those described in Example 5. The formulations represent further examples of artificial tear compositions containing bis-amine compounds in accordance with the present invention.

TABLE 3

| Component | Concentration (% w/v) | | | | | |
|---|---|---|---|---|---|---|
| | 11398-40A | 11398-40B | 11398-40C | 11398-40E | 11398-40F | 11398-40G |
| AMP (95%) | 0.588$^a$ | | | | | |
| AL-38571A | | 2.0$^a$ | | | | |
| AL-39586 | | | 2.1$^a$ | | | |
| AL-39504 | | | | 2.3$^a$ | | |
| AL-39503 | | | | | 2.1$^a$ | |
| Dextran 70 | 0.1 | 0.1 | 0.1 | 0.1 | 0.1 | 0.1 |
| HPMC | 0.3 | 0.3 | 0.3 | 0.3 | 0.3 | 0.3 |
| Propylene glycol | 0.3 | 0.3 | 0.3 | 0.3 | 0.3 | 0.3 |
| Boric acid | 0.8 | 0.8 | 0.8 | 0.8 | 0.8 | 0.8 |
| Sorbitol | 1.4 | 1.4 | 1.4 | 1.4 | 1.4 | 1.4 |
| Sodium chloride | 0.05 | 0.05 | 0.05 | 0.05 | 0.05 | 0.05 |
| Potassium chloride | 0.05 | 0.05 | 0.05 | 0.05 | 0.05 | 0.05 |
| Calcium chloride | 0.0053 | 0.0053 | 0.0053 | 0.0053 | 0.0053 | 0.0053 |
| Magnesium chloride | 0.0064 | 0.0064 | 0.0064 | 0.0064 | 0.0064 | 0.0064 |
| Zinc chloride | 0.00015 | 0.00015 | 0.00015 | 0.00015 | 0.00015 | 0.00015 |
| pH | 7.9 | 7.9 | 7.9 | 7.9 | 7.9 | 7.9 |

$^a$The concentrations of AMP and the bis-amines shown here are equimolar (i.e., 70 mM).

EXAMPLE 8

The antimicrobial activity of the solutions described in Example 7 was evaluated by means of a standard microbiological analysis (i.e., USP 27 Antimicrobial Effectiveness Test). The results are presented in Table 4 below:

TABLE 4

| Microorganism | Time (days) | Log₁₀ Reduction of Survivors | | | | | |
|---|---|---|---|---|---|---|---|
| | | 11398-40A | 11398-40B | 11398-40C | 11398-40E | 11398-40F | 11398-40G |
| A. niger | 7 | 2.4 | 2.9 | 2.6 | 2.4 | 3.3 | 2.5 |
| $4.4 \times 10^{5a}$ | 14 | 3.1 | 3.2 | 3.2 | 2.4 | 3.8 | 2.3 |
| | 28 | <u>5.6</u>[b] | 4.9 | 4.5 | 3.6 | <u>5.6</u> | 3.8 |
| C. albicans | 7 | 0.5 | 0.1 | 0.3 | 0.3 | 0.9 | 0.1 |
| $9.8 \times 10^5$ | 14 | 2.3 | 1.3 | 1.4 | 0.4 | 2.0 | 0.4 |
| | 28 | <u>6.0</u> | 2.2 | 3.4 | 1.7 | <u>6.0</u> | 2.1 |
| E. coli | 7 | 1.5 | 4.8 | 4.0 | 3.3 | 3.2 | 4.1 |
| $6.1 \times 10^5$ | 14 | 3.3 | <u>5.8</u> | <u>5.8</u> | 3.4 | <u>5.8</u> | 2.2 |
| | 28 | <u>5.8</u> | <u>5.8</u> | <u>5.8</u> | 3.4 | <u>5.8</u> | −0.7 |
| P. aeruginosa | 7 | 0.9 | <u>6.0</u> | <u>6.0</u> | 2.4 | 4.9 | 4.5 |
| $1.1 \times 10^6$ | 14 | 1.7 | 5.3 | <u>6.0</u> | 0.0 | <u>6.0</u> | 4.3 |
| | 28 | 4.5 | <u>6.0</u> | 5.3 | 0.0 | <u>6.0</u> | 3.7 |
| S. aureus | 7 | 2.4 | 1.2 | 1.4 | 4.1 | <u>5.9</u> | <u>5.9</u> |
| $8.4 \times 10^5$ | 14 | 5.2 | 3.2 | <u>5.9</u> | <u>5.9</u> | <u>5.9</u> | <u>5.9</u> |
| | 28 | <u>5.9</u> | <u>5.9</u> | <u>5.9</u> | <u>5.9</u> | <u>5.9</u> | 4.7 |

11239:021

[a]Initial inoculum control count
[b]Underlined number indicates no survivors (<10 CFU/mL) recovered

We claim:

1. A sterile aqueous ophthalmic composition comprising a bis-amine of the following formula, in an amount effective to enhance the antimicrobial activity of the composition:

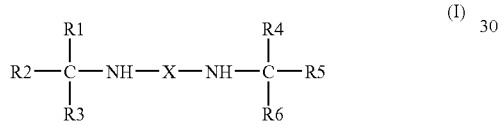

(I)

wherein:
$R_1, R_2, R_3, R_4, R_5$ and $R_6$ are independently selected from the group consisting of:
H; —CH$_2$OH; and C$_1$-C$_5$ straight or branched alkyl or alkenyl, optionally containing one or more heteroatoms, provided that no more than one of R1, R2 and R3 is —CH$_2$OH, and no more than one of R4, R5 and R6 is —CH$_2$OH; and X is (—CH$_2$—)$_w$CHOH—CHOH(—CH$_2$—)$_w$, wherein w is a whole number of from 1 to 6 and the hydroxy groups are in either cis or trans configurations;
or a pharmaceutically acceptable salt thereof, said composition having a physiologically compatible pH and an osmolality of 210 to 320 mOsm/kg.

2. A composition according to claim 1, wherein the bis-amine of formula (I) is 1,4-bis[isobutylamino]2,3-dihydroxy butane.

3. A method of enhancing the antimicrobial activity of a sterile, aqueous pharmaceutical composition, which comprises including an effective amount of a bis-amine in the composition, said bis-amine having the formula:

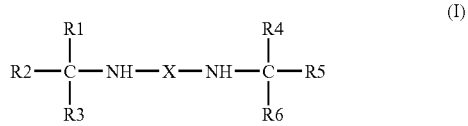

(I)

wherein:
$R_1, R_2, R_3, R_4, R_5$ and $R_6$ are independently selected from the group consisting of:
H; —CH$_2$OH; and C$_1$-C$_5$ straight or branched alkyl or alkenyl, optionally containing one or more heteroatoms, provided that no more than one of R1, R2 and R3 is —CH$_2$OH, and no more than one of R4, R5 and R6 is —CH$_2$OH; and X is (—CH$_2$)$_w$—CHOH—CHOH(—CH$_2$—)$_w$, wherein w is a whole number of from 1 to 6 and the hydroxy groups are in either cis or trans configurations;
or a pharmaceutically acceptable salt thereof.

4. A method according to claim 3, wherein the bis-amine of formula (I) is 1,4-bis[isobutylamino]2,3-dihydroxy butane.

5. The composition of claim 1 further comprising a borate.

6. The method of claim 3 wherein the composition further comprises a borate.

7. The composition of claim 1 further comprising at least one additional antimicrobial activity enhancing agent.

8. The composition of claim 7, wherein the at least one additional antimicrobial activity enhancing agent is either an amidoamine or an amino alcohol.

9. The composition of claim 7, wherein the at least one additional antimicrobial activity enhancing agent is selected from the group consisting of myristamidopropyl dimethylamine and 2-amino-2-methyl-1-propanol.

10. The method of claim 3 wherein the composition further comprises at least one additional antimicrobial activity enhancing agent.

11. The method of claim 10, wherein the at least one additional antimicrobial activity enhancing agent is either an amidoamine or an amino alcohol.

12. The method of claim 10, wherein the at least one additional antimicrobial activity enhancing agent is selected from the group consisting of myristamidopropyl dimethylamine and 2-amino-2-methyl-1-propanol.

13. The composition of claim 1 further comprising at least one antimicrobial agent.

14. The composition of claim 13, wherein the at least one antimicrobial agent is selected from the group consisting of polyquaternium-1 and polyhexamethylene biguanide.

15. The method of claim 3, wherein the composition further comprises at least one antimicrobial agent.

16. The method of claim 15, wherein the at least one antimicrobial agent is selected from the group consisting of polyquaternium-1 and polyhexamethylene biguanide.

* * * * *